(12) United States Patent
Souvie et al.

(10) Patent No.: US 7,999,129 B2
(45) Date of Patent: *Aug. 16, 2011

(54) PROCESS FOR THE SYNTHESIS OF (7-METHOXY-1-NAPHTHYL) ACETONITRILE AND ITS APPLICATION IN THE SYNTHESIS OF AGOMELATINE

(75) Inventors: Jean-Claude Souvie, Le Havre (FR); Isaac Gonzalez Blanco, Toledo (ES)

(73) Assignee: Les Laboratoires Servier, Suresnes Cedex (FR)

( * ) Notice: Subject to any disclaimer, the term of this patent is extended or adjusted under 35 U.S.C. 154(b) by 312 days.

This patent is subject to a terminal disclaimer.

(21) Appl. No.: 12/315,983

(22) Filed: Dec. 9, 2008

(65) Prior Publication Data

US 2009/0131719 A1 May 21, 2009

Related U.S. Application Data

(62) Division of application No. 11/052,629, filed on Feb. 7, 2005, now Pat. No. 7,476,751.

(30) Foreign Application Priority Data

Feb. 13, 2004 (FR) ...................... 04 01438

(51) Int. Cl.
*C07C 253/04* (2006.01)
*C07C 231/02* (2006.01)
*C07C 233/02* (2006.01)

(52) U.S. Cl. .................. 558/351; 564/130; 564/172

(58) Field of Classification Search .................. 564/172, 564/130; 558/351
See application file for complete search history.

(56) References Cited

U.S. PATENT DOCUMENTS

| 3,931,188 | A | 1/1976 | Douglas et al. |
| 3,992,403 | A | 11/1976 | Roebke |
| 7,250,531 | B2 | 7/2007 | Souvie et al. ................. 564/172 |
| 7,544,839 | B2 * | 6/2009 | Souvie et al. ................. 564/172 |
| 2005/0182268 | A1 | 8/2005 | Souvie et al. ................. 558/357 |

FOREIGN PATENT DOCUMENTS

EP 0447285 9/1991

OTHER PUBLICATIONS

*French Search Report for French Application No. 04.01438*, Sep. 14, 2004.
*European Search Report for European Application No. 05290307*, May 20, 2005.
*International Search Report for International Application No. PCT/FR2005/000326*, Jun. 16, 2005.
Depreux, et al., *J. Med. Chem.*, 1994, 37, 3231-3239.

* cited by examiner

*Primary Examiner* — James O Wilson
*Assistant Examiner* — Ebenezer O Sackey
(74) *Attorney, Agent, or Firm* — Hueschen and Sage

(57) ABSTRACT

A process for the industrial synthesis of the compound of formula (I)

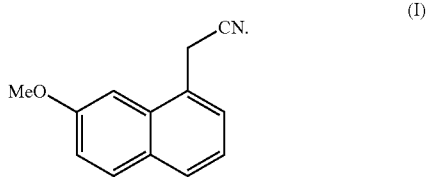

(I)

Application in the synthesis of agomelatine.

1 Claim, No Drawings

US 7,999,129 B2

PROCESS FOR THE SYNTHESIS OF (7-METHOXY-1-NAPHTHYL) ACETONITRILE AND ITS APPLICATION IN THE SYNTHESIS OF AGOMELATINE

FIELD OF THE INVENTION

The present invention relates to a process for the industrial synthesis of (7-methoxy-1-naphthyl)acetonitrile and to its application in the industrial production of agomelatine, or N-[2-(7-methoxy-1-naphthyl)ethyl]acetamide.

More specifically, the present invention relates to a process for the industrial synthesis of the compound of formula (I):

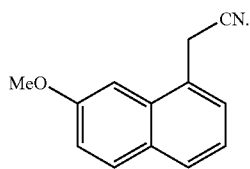

(I)

The compound of formula (I) obtained according to the process of the invention is useful in the synthesis of agomelatine, or N-[2-(7-methoxy-1-naphthyl)ethyl]acetamide, of formula (II):

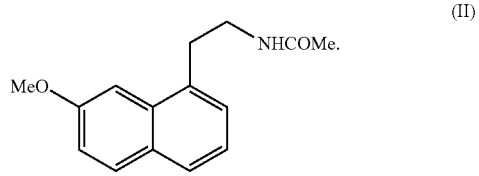

(II)

BACKGROUND OF THE INVENTION

Agomelatine, or N-[2-(7-methoxy-1-naphthyl)ethyl]acetamide, has valuable pharmacological properties.

Indeed it has the double feature of being, on the one hand, an agonist of melatoninergic system receptors and, on the other hand, an antagonist of the 5-HT$_{2C}$ receptor. Those properties confer activity in the central nervous system and, more especially, in the treatment of severe depression, seasonal affective disorders, sleep disorders, cardiovascular pathologies, pathologies of the digestive system, insomnia and fatigue resulting from jetlag, appetite disorders and obesity.

DESCRIPTION OF THE PRIOR ART

Agomelatine, its preparation and its therapeutic use have been described in European Patent Specification EP 0 447 285.

In view of the pharmacological value of this compound, it has been important to be able to obtain it by an effective industrial synthesis process that is readily transposable to an industrial scale and that results in agomelatine in a good yield and with excellent purity.

Patent Specification EP 0 447 285 describes the preparation of agomelatine in eight steps, starting from 7-methoxy-1-tetralone, giving an average yield of less than 30%.

That process involves the action of ethyl bromoacetate, followed by aromatisation and saponification to yield the corresponding acid, which is then converted to acetamide and subsequently dehydrated to yield (7-methoxy-1-naphthyl)acetonitrile, this being followed by reduction, and then condensation of the acetyl chloride.

In particular, the preparation of (7-methoxy-1-naphthyl) acetonitrile involves six reaction steps and, transposed to an industrial scale, has quickly demonstrated the difficulties of carrying out the process, these being caused principally by problems of reproducibility of the first step, which constitutes the action of ethyl bromoacetate on 7-methoxy-1-tetralone according to the Réformatsky reaction resulting in ethyl (7-methoxy-3,4-dihydro-1(2H)-naphthalenylidene)ethanoate.

Moreover, the subsequent step of aromatisation of ethyl (7-methoxy-3,4-dihydro-1(2H)-naphthalenylidene)ethanoate has often been incomplete and resulted, after saponification, in a mixture of products that is difficult to purify.

The literature describes obtaining (7-methoxy-1-naphthyl) acetonitrile in three steps starting from 7-methoxy-1-tetralone, by the action of LiCH$_2$CN followed by dehydrogenation with DDQ (2,3-dichloro-5,6-dicyano-1,4-benzoquinone) and finally dehydration in acid medium (Synthetic Communication, 2001, 31(4), 621-629). The total yield is mediocre (76%), however, and in particular the DDQ used in the dehydrogenation reaction and the benzene reflux necessary in the third step do not comply with industrial requirements in terms of cost and the environment.

DETAILED DESCRIPTION OF THE INVENTION

The Applicant has now developed a new industrial synthesis process that results, in a reproducible manner and without the need for laborious purification, in agomelatine of a purity compatible with its use as a pharmaceutical active ingredient.

An alternative to the difficulties encountered with the process described in Patent Specification EP 0 447 285 has been obtained by directly condensing a cyano compound with 7-methoxy-1-tetralone. It was in addition necessary that the condensation compound obtained could readily be subjected to aromatisation to yield (7-methoxy-1-naphthyl)acetonitrile without the need for drastic conditions, and that reagents compatible with industrial requirements in terms of cost and the environment could be used.

It is apparent that (7-methoxy-3,4-dihydro-1-naphthalenyl)acetonitrile would constitute an ideal synthesis intermediate that meets the requirements for direct synthesis from 7-methoxy-1-tetralone, and would be an excellent substrate for the aromatisation step.

Reactions for the direct condensation of tetralones with acetonitrile or acetonitrile compounds are described in the literature. In particular, U.S. Pat. No. 3,992,403 describes the condensation of cyanomethyl phosphonate with 6-fluoro-1-tetralone, and U.S. Pat. No. 3,931,188 describes the condensation of acetonitrile with tetralone leading to a cyano intermediate which is directly engaged in the subsequent reaction. Applied to 7-methoxy-1-tetralone, the condensation of acetonitrile yields a mixture of isomers in which "exo" constitutes the major portion and "endo" the minor portion, according to FIG. 1:

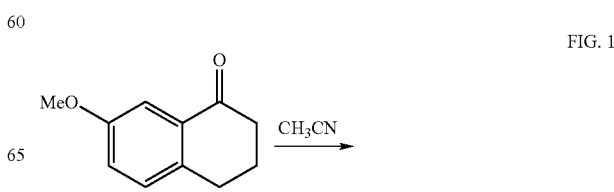

FIG. 1

-continued

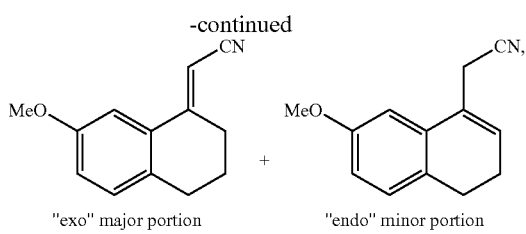

"exo" major portion    "endo" minor portion obtaining such a mixture requiring subsequent drastic aromatisation conditions that are not compatible with the industrial requirements for the purpose of carrying out the synthesis of agomelatine.

The Applicant has now developed a new industrial synthesis process that allows (7-methoxy-1-naphthyl)acetonitrile to be obtained from 7-methoxy-tetralone, in a reproducible manner and without the need for laborious purification, in only two steps by using as synthesis intermediate (7-methoxy-3,4-dihydro-1-naphthalenyl)acetonitrile free from the "exo" impurity of formula (III):

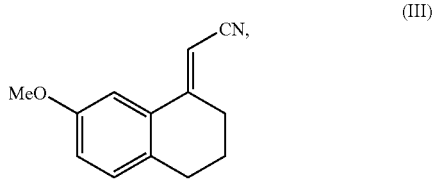
(III)

which impurity cannot be subjected to subsequent aromatisation under operating conditions that are compatible with the industrial requirements for the purpose of carrying out the synthesis of agomelatine.

More specifically, the present invention relates to a process for the industrial synthesis of the compound of formula (I):

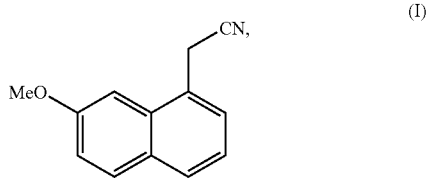
(I)

which is characterised in that 7-methoxy-1-tetralone of formula (IV):

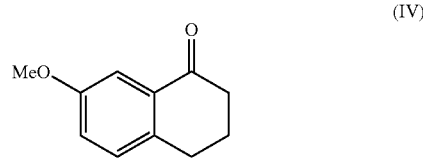
(IV)

is reacted with cyanoacetic acid of formula (V):

(V)

in conditions wherein the water formed is removed, in the presence of a catalytic amount of a compound of formula (VI):

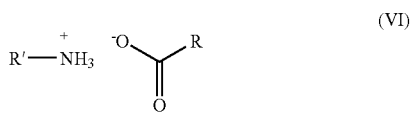
(VI)

wherein R and R', which may be the same or different, each represents a linear or branched ($C_3$-$C_{10}$)alkyl group, an unsubstituted or substituted aryl group, or an unsubstituted or substituted linear or branched aryl ($C_1$-$C_6$)alkyl group, to yield, after filtration and washing with a basic solution, (7-methoxy-3,4-dihydro-1-naphthalenyl)acetonitrile of formula (VII):

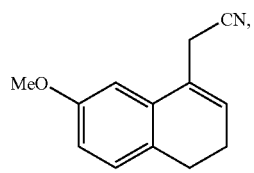
(VII)

which compound of formula (VII) is reacted with a hydrogenation catalyst in the presence of an allyl compound, to yield the compound of formula (I) after filtration and removal of the solvent by evaporation, which compound of formula (I) is isolated in the form of a solid after recrystallisation wherein:
  aryl is understood to mean a phenyl, naphthyl or biphenyl group,
  the term "substituted" governing the terms "aryl" and "arylalkyl" denotes that the aromatic moiety of those groups may be substituted by from 1 to 3 identical or different groups selected from linear or branched ($C_1$-$C_6$)alkyl, hydroxy and linear or branched ($C_1$-$C_6$)alkoxy,
  "allyl compound" is understood as any molecule containing from 3 to 10 carbon atoms, which may contains in addition 1 to 5 oxygen atoms, and containing at least one —$CH_2$—CH=$CH_2$ group.

More especially, in the reaction for the conversion of the compound of formula (IV) to a compound of formula (VII), the water formed is removed by distillation. There is preferably used a reaction solvent that has a boiling temperature higher than or equal to that of water, and even more preferably that forms an azeotrope with water, such as, for example, xylene, toluene, anisole, ethylbenzene, tetrachloroethylene, cyclohexene or mesitylene.

Preferably, the conversion of the compound of formula (IV) to the compound of formula (VII) is carried out with reflux of toluene or xylene and, more especially, with reflux of toluene.

In the reaction for the conversion of the compound of formula (IV) to a compound of formula (VII), advantageously one of the groups R or R' of the catalyst employed represents a linear or branched ($C_3$-$C_{10}$)alkyl group and the other represents an aryl or arylalkyl group. More especially, a preferred catalyst is that of formula ($VI_a$):

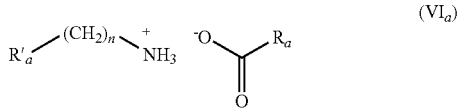

(VI$_a$)

wherein R'$_a$ represents a phenyl group unsubstituted or substituted by one or more linear or branched (C$_1$-C$_6$)alkyl groups, n is 0 or 1, and R$_a$ represents a linear (C$_3$-C$_{10}$)alkyl group.

Advantageously, R'$_a$ represents an unsubstituted or substituted phenyl group, more especially an unsubstituted phenyl group.

The preferred group R$_a$ is the hexyl group.

Advantageously, n is 1.

The preferred catalyst used in the conversion of the compound of formula (IV) to the compound of formula (VII) according to the process of the invention is benzylammonium heptanoate of formula (VIII):

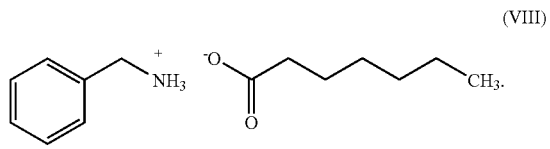

(VIII)

Advantageously, the compound of formula (VII) is obtained after filtration and washing with a mineral or organic basic solution, such as NaOH, KOH, Ca(OH)$_2$, Sr(OH)$_2$ or NH$_4$OH, and more especially with a sodium hydroxide solution.

Preferably, the conversion of the compound of formula (VII) to the compound of formula (I) is carried out with reflux of toluene or xylene, more especially with reflux of toluene.

The catalyst preferably used in the conversion of the compound of formula (VII) to the compound of formula (I) is a catalyst either in oxide form or supported as for example palladium, platinum, nickel, Al$_2$O$_3$ and, more especially, palladium. Advantageously, 1 to 20% palladium-on-carbon will be used, and more particularly 5% or 10% palladium-on-carbon. Preferably, palladium-on-carbon will be used in amounts ranging from 1 to 10% by weight of catalyst in relation to the weight of substrate, and more especially 5%. The hydrogen acceptor preferably used in the reaction for the conversion of the compound of formula (VII) to a compound of formula (I) is an allyl compound and, more especially, an allyl acrylate or an allyl glycidyl ether. The preferred allyl acrylate of the process according to the invention is allyl methacrylate.

This process is of particular interest for the following reasons:
  it allows the "endo" compound of formula (VII), exclusively, to be obtained on an industrial scale. This result is altogether surprising considering the literature relating to that type of reaction, which most frequently reports obtaining "exo"/"endo" mixtures (Tetrahedron, 1966, 22, 3021-3026). The result is due to the use of a compound of formula (VI) as reaction catalyst instead of the ammonium acetates currently used in such reactions (Bull. Soc. Chim. Fr., 1949, 884-890).
  the rate of conversion of the compound of formula (IV) to the compound of formula (VII) is very high, exceeding 97%, unlike that which could be observed using acetic acid, for which the rate does not exceed 75%.
  the use of a hydrogenation catalyst in the presence of an allyl compound for the conversion of the compound of formula (VII) to the compound of formula (I) is entirely compatible with industrial requirements in terms of cost and the environment, unlike the quinones currently used.
  furthermore, it allows the compound of formula (I), exclusively, in particular free from the corresponding reduction product of formula (IX):

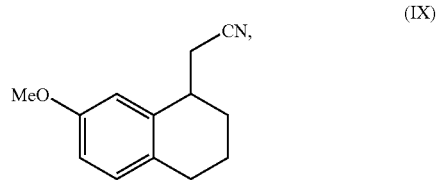

(IX)

to be obtained on an industrial scale.
  finally, the observed rates of conversion of the compound of formula (VII) to the compound of formula (I) are high, exceeding 90%.

The compound of formula (VII) obtained according to the process of the invention is new and is useful as an intermediate in the synthesis of agomelatine, in which it is subjected to aromatisation followed by reduction and then to coupling with acetic anhydride.

The compound of formula (I) so obtained is, if necessary, subjected to reduction and then to coupling with acetic anhydride to yield agomelatine.

The Examples below illustrate the invention but do not limit it in any way.

EXAMPLE 1

(7-Methoxy-1-naphthyl)acetonitrile

Step A: (7-Methoxy-3,4-dihydro-1-naphthalenyl)acetonitrile

There are introduced into a 670 liter reactor 85.0 kg of 7-methoxy-1-tetralone, 60.3 kg of cyanoacetic acid and 15.6 kg of heptanoic acid in toluene in the presence of 12.7 kg of benzylamine. The mixture is heated at reflux. When all the starting substrate has disappeared, the solution is cooled and filtered. The precipitate obtained is washed with toluene and then the filtrate obtained is washed with a 2N sodium hydroxide solution and subsequently with water until neutral. After removal of the solvent by evaporation, the resulting solid is recrystallised from an ethanol/water (80/20) mixture to give the title product in a yield of 90% and with a chemical purity exceeding 99%.

Melting point: 48-50° C.

Step B: (7-Methoxy-1-naphthyl)acetonitrile

There are introduced into a 670 liter reactor 12.6 kg of 5% palladium-on-carbon in toluene, which is heated at reflux; then 96.1 kg of (7-methoxy-3,4-dihydro-1-naphthalenyl)-acetonitrile dissolved in toluene are added as well as 63.7 kg of allyl methacrylate. The reaction is continued at reflux and is followed by vapour phase chromatography. When all the starting substrate has disappeared, the reaction mixture is cooled to ambient temperature and then filtered. After removal of the toluene by evaporation, the resulting solid residue is recrystallised from an ethanol/water (80/20) mixture to give the title product in a yield of 91% and with a chemical purity exceeding 99%.

Melting point: 83° C.

EXAMPLE 2

(7-Methoxy-1-naphthyl)acetonitrile

Step A: (7-Methoxy-3,4-dihydro-1-naphthalenyl)acetonitrile

There are introduced into a 670 liter reactor 85.0 kg of 7-methoxy-1-tetralone, 60.3 kg of cyanoacetic acid and 15.6 kg of heptanoic acid in toluene in the presence of 11.0 kg of aniline. The mixture is heated at reflux. When all the starting substrate has disappeared, the solution is cooled and filtered. The precipitate obtained is washed with toluene and then the filtrate obtained is washed with a 2N sodium hydroxide solution, and subsequently with water until neutral. After removal of the solvent by evaporation, the resulting solid is recrystallised from an ethanol/water (80/20) mixture to give the title product in a yield of 87% and with a chemical purity exceeding 99%.

Melting, point: 48-50° C.

Step B: (7-Methoxy-1-naphthyl)acetonitrile
The procedure is as in Step B of Example 1.

We claim:

1. A process for the synthesis of agomelatine, wherein 7-methoxy-1-tetralone of formula (IV):

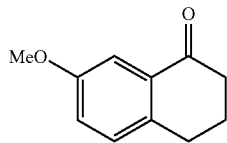

(IV)

is reacted with cyanoacetic acid of formula (V):

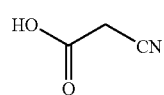

(V)

wherein the water formed during the reaction is removed, in the presence of a catalytic amount of a compound of formula (VI):

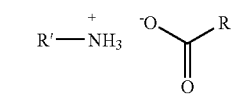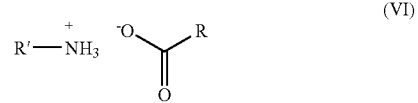

(VI)

wherein R and R', which may be the same or different, each represents linear or branched $(C_3-C_{10})$alkyl, unsubstituted or substituted aryl, or unsubstituted or substituted linear or branched aryl $(C_1-C_6)$alkyl, to yield, after filtration and washing with a basic solution, (7-methoxy-3,4-dihydro-1-naphthalenyl)acetonitrile of formula (VII):

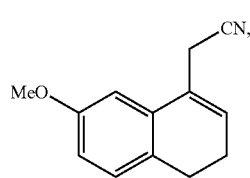

(VII)

which compound of formula (VII) is subjected to aromatisation followed by reduction and then to coupling with acetic anhydride to yield agomelatine, it being understood that:
aryl may be phenyl, naphthyl or biphenyl, and
the term substituted associated with the terms aryl and arylalkyl denotes that the aromatic moiety of those groups may be substituted by one or more, identical or different, groups selected from linear or branched $(C_1-C_6)$alkyl, hydroxy and linear or branched $(C_1-C_6)$ alkoxy.

* * * * *

UNITED STATES PATENT AND TRADEMARK OFFICE
CERTIFICATE OF CORRECTION

| | |
|---|---|
| PATENT NO. | : 7,999,129 B2 |
| APPLICATION NO. | : 12/315983 |
| DATED | : August 16, 2011 |
| INVENTOR(S) | : Jean-Claude Souvie et al. |

It is certified that error appears in the above-identified patent and that said Letters Patent is hereby corrected as shown below:

Cover Page, Assignee: "Les Laboratories Servier" should be --Les Laboratoires Servier--.

Signed and Sealed this
Eighteenth Day of October, 2011

David J. Kappos
*Director of the United States Patent and Trademark Office*